United States Patent [19]
Webb

[11] Patent Number: 5,709,648
[45] Date of Patent: Jan. 20, 1998

[54] RESILIENT BACK SUPPORT DEVICE

[75] Inventor: Joseph Walter Webb, 248 Huckleberry Trail, Woodside, Calif. 94062

[73] Assignee: Joseph Walter Webb, Woodside, Calif.

[21] Appl. No.: 710,522

[22] Filed: Sep. 18, 1996

[51] Int. Cl.[6] .................................................. A61F 5/00
[52] U.S. Cl. .................................................. 602/19; 2/44
[58] Field of Search .......................... 620/18, 19, 20; 128/869, 873-875; 2/44, 45, 69

[56] References Cited

U.S. PATENT DOCUMENTS

| | | | |
|---|---|---|---|
| 421,635 | 2/1890 | Teufel | 602/19 |
| 903,403 | 11/1908 | Quick | 602/19 |
| 1,008,500 | 11/1911 | Thornton | 602/19 |
| 1,202,851 | 10/1916 | Kelly | 2/44 |
| 1,409,326 | 3/1922 | Williamson | 2/44 |
| 1,812,529 | 6/1931 | Haulbrook | 602/19 |
| 3,292,616 | 12/1966 | Freeman | 602/19 |
| 3,570,011 | 3/1971 | Naig | 2/44 |
| 3,897,776 | 8/1975 | Gaylord, Jr. | 602/19 |
| 4,608,716 | 9/1986 | Brumfield | 2/2.5 |
| 4,829,989 | 5/1989 | Deamer et al. | 602/19 |
| 5,007,412 | 4/1991 | DeWall | 602/19 |
| 5,176,622 | 1/1993 | Anderson et al. | 602/19 |
| 5,465,424 | 11/1995 | Cudney | 2/2 |
| 5,553,322 | 9/1996 | Cebo-Johnson | 2/69 |
| 5,582,583 | 12/1996 | Ballantyne | 602/23 |
| 5,606,745 | 3/1997 | Gray | 2/69 |

*Primary Examiner*—Richard J. Apley
*Assistant Examiner*—Denise Pothier
*Attorney, Agent, or Firm*—John S. Heyman

[57] ABSTRACT

A back support device employs a torso covering sheet (18) having a plurality of resilient stiffening rods (20), a torso harness consisting a shoulder straps (10), an abdominal strap (12), a breast strap (22), and leg straps (14). The torso harness encompasses the entire back and buttocks of the wearer and its base attaches to the upper leg or thigh. The resilient stiffening rods (20) are placed in sleeves (16) sewn on the long axis of the torso covering sheet (18). When the user bends over the resilient stiffening rods (20) transfer load away from the lower back, and onto the large muscles of the upper leg, thereby relieving stress on the user's back.

5 Claims, 3 Drawing Sheets

FIG. 3
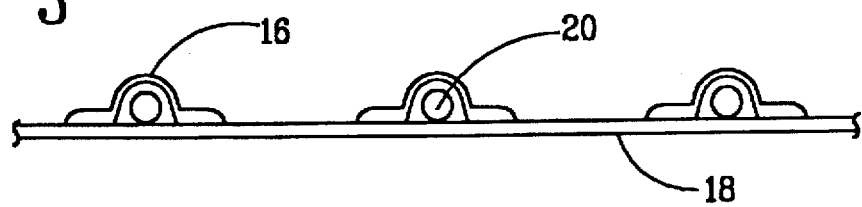
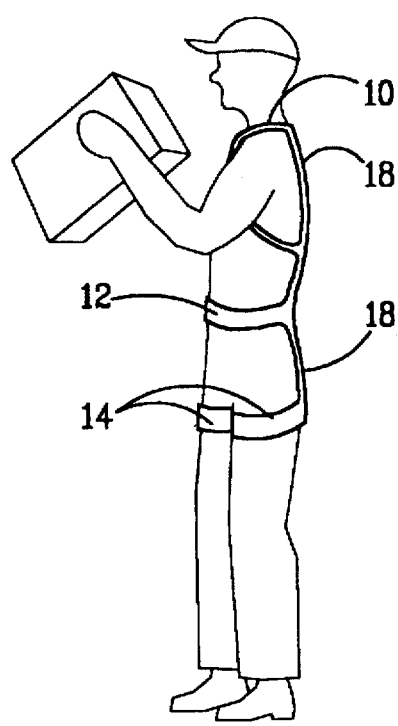
FIG. 4
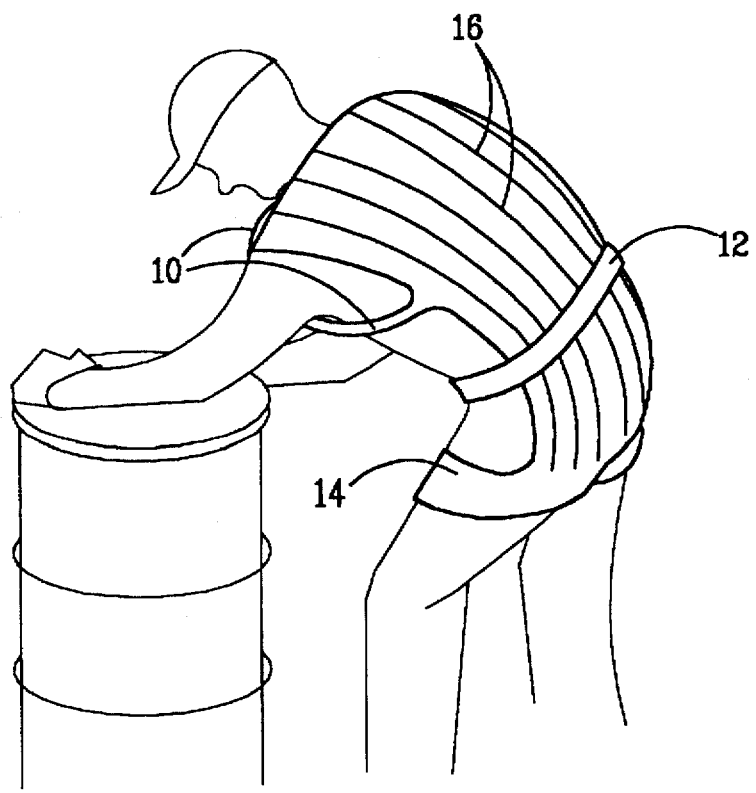
FIG. 5

RESILIENT BACK SUPPORT DEVICE

BACKGROUND

1. Field of Invention

This invention relates to relief and prevention of back strain or injury in the human body, specifically to an appliance worn on the torso to effect such relief and prevention.

BACKGROUND

2. Description of Prior Art

There are many appliances available for back support, most of which brace or hold the back, often in combination with the abdomen or chest, through means of a binding with fabric or plastic material. There are others utilizing elastic straps. Still others employ mechanical devices, even motors, to provide traction and load shifting.

One device, shown in U.S. Pat. No. 5,176,622 to Anderson et al; Jan. 5, 1993, utilizes springs to relieve strain from bending over.

These devices are complicated and cumbersome, uncomfortable, of questionable utility, and not designed to respond differently to differing conditions of kinetic demand, i.e., ordinary human body movements, such as bending over as opposed to walking.

Objects and Advantages

Accordingly, several objects and advantages of my invention provide back support which:

a) comes into operation only when the user begins to bend over, in any direction;
b) affords freedom from any unnecessary loading or binding;
c) is elegantly simple in design;
d) is very inexpensive and virtually universally available;
e) provides versatility and adjustibility.
f) still further objects and advantages are that my back support device provides dramatic back support which is variable, the user can choose the amount of support by changing the size of one component; it is extremely lightweight; it can compensate 100% for both the weight of the torso and the weight of an object being lifted, thus completely neutralizing load on back muscles.

In sum, my back support device is not a partial remedy for back loading. It offers complete elimination of load on the back muscles. And this, of course, will relieve strain and stress on a previously injured back, and will prevent further injury. Thus, my back support device provides both prevention and partial cure.

DRAWING FIGURES

FIG. 3 shows a sectional view of my back support device, with resilient rods and sleeves.

FIG. 4 shows a user standing with my back support device.

FIG. 5 shows a user bending over with loaded resilient rods and sleeves.

Figure 1:
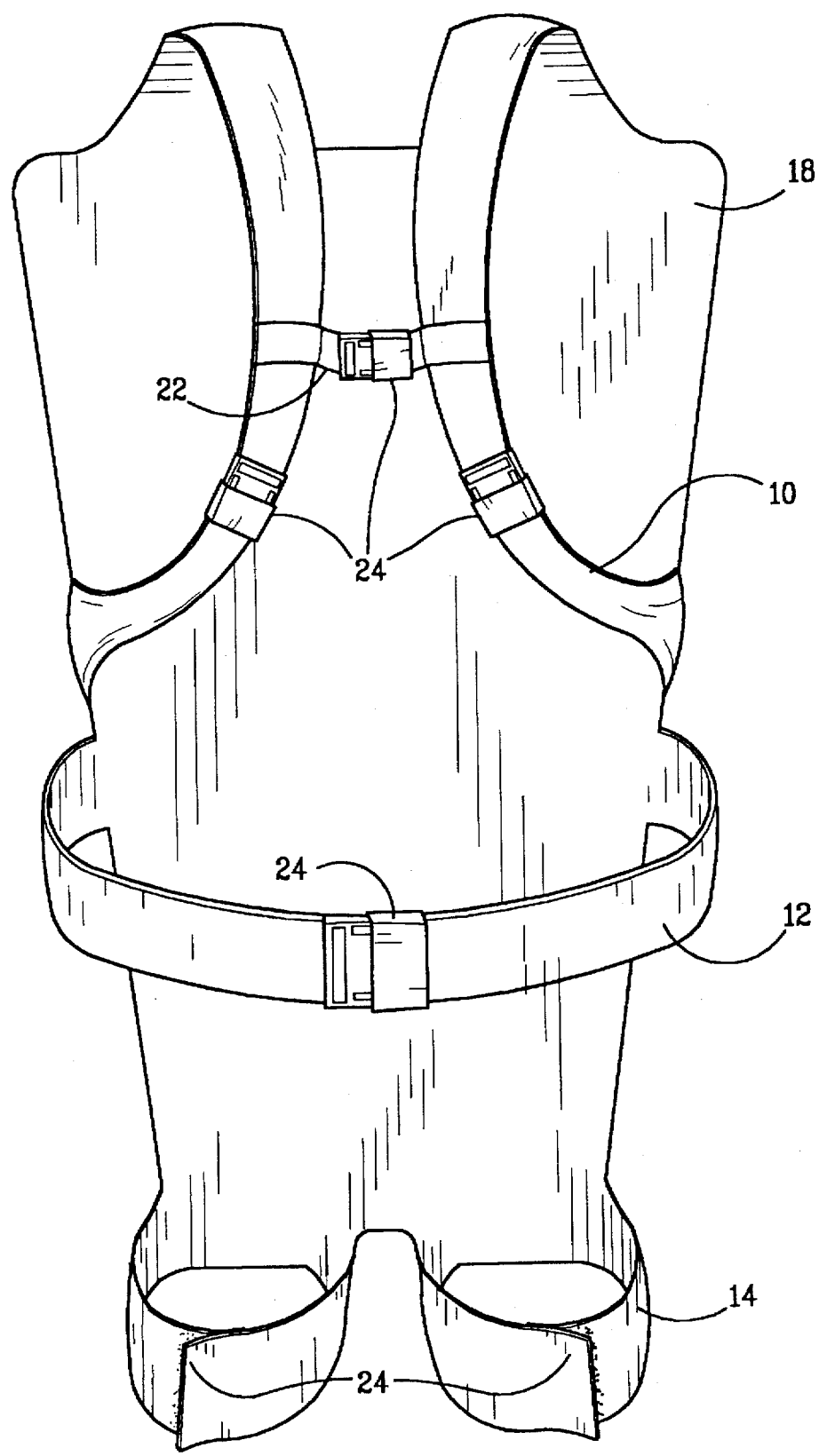
FIG. 1 shows a front view of a back support device with straps in accordance with my invention.

Reference Numerals In Drawings 10 shoulder strap
12 abdominal strap
14 leg strap
16 sleeves (receive resilient rods)
18 fabric body
20 resilient rods
22 breast strap
24 quick release fasteners
26 rod securing flap

SUMMARY

A resilient back support device for the torso comprising a sheet of flexible mesh material which fits over the back and buttocks, with affixing means to reduce or eliminate back strain.

Figure 2:
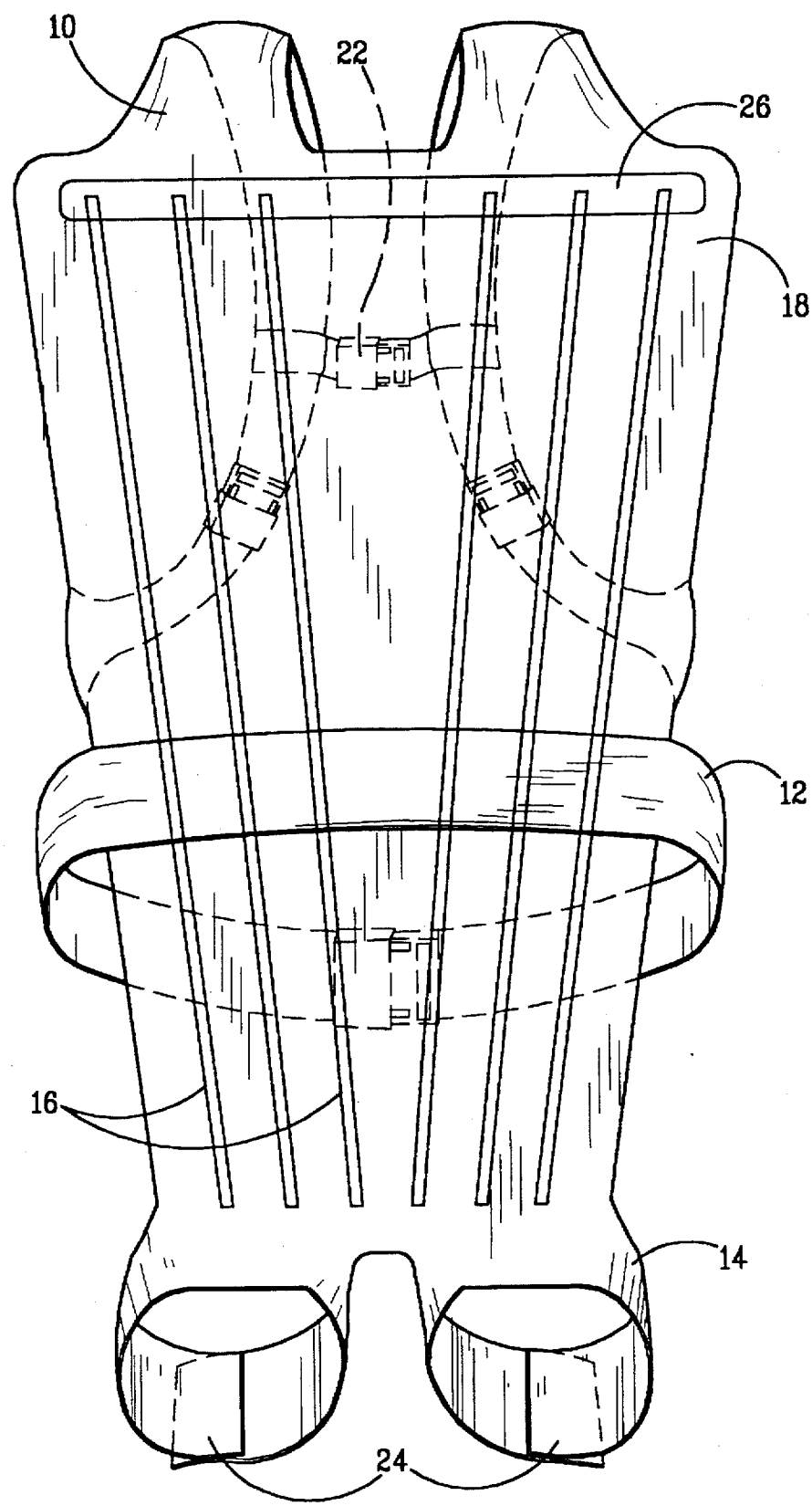
FIG. 2 shows a rear view of my back support device, with resilient rods and sleeves.

Description—FIGS. 1 and 2

My back support device comprises a fabric body 18 (FIG. 1), of a generally rectangular shape, extending from the top of the shoulders to below the buttocks. Straps 10, 12, 14 secure fabric body 18 to the wearer's legs, abdomen, chest and shoulders. Several fabric sleeves 16 (FIG. 2), arranged on the long axis of fabric body 18 accept respective resilient rods 20. When the user bends over, the rods resist movement and transfer the load away from the back and onto the upper legs.

Straps 10 are shoulder straps which run from top of upper end of fabric body 18 (approximately 4 cm from the top corners) over the shoulders, down the breast, under the arms, and finally fasten to fabric body 18 approximately 37 cm from top corners of fabric body 18 at about waist level. Strap 12 is an abdominal strap which extends around the abdomen and fastens at the center of fabric body 18 in the back. Abdominal strap 12 rides on top of, or covers the resilient rods and sleeves thus cinching them in snugly to the small of the back. Straps 14 are leg strap's which have nylon padding across the front and on top of the quadriceps; they embrace the upper thigh. A breast strap 22 connects shoulder straps 10 across the sternum. All straps preferably are attached to each other and to body 18 by sewing.

All straps employ quick release fasteners 24. Quick release fasteners allow rapid disengagement or adjustment so as to accomodate body movements such as kneeling or squatting. All of the straps preferably are made of nylon. Shoulder straps 10 are about 10 cm wide. Abdominal straps 12 and breast straps 22 are about 7 cm wide. Leg straps 14 are about 20 cm wide.

Operation—FIG. 1

Straps 10, 12, and 14 work as a harness to fasten the torso to the upper legs. The key component of this fastening is the complement of resilient rods 20 and sleeves 16 of FIG. 2, which will now be discussed.

Description—FIG. 2

FIG. 2 shows sleeves 16 housing resilient rods 20. All materials are preferably nylon fabric, except for the rods, which are preferably fiberglass. A flap 26 (FIG. 2) over the tops of the rods secures them in place.

Operation—FIG. 2

The combination of resilient rods 20 and sleeves 16, when secured in place by fabric body 18, operate as a load shifter. The load on the lower back, when bending over, is transferred, via the resilient rods, to the strong quadriceps muscles of the upper thigh. As one bends over, the rods are bent and the load is delivered to their bases. The bases of rods 20 are anchored at the bottom of fabric body 18. As rods 20 are bent, the load is thus transferred to leg straps 14 and the upper legs assume the load and remain loaded as long as one bends over. Most importantly, resilient rods 20, thus loaded, assist the user in returning to the upright standing posture without back strain. A set of differently sized rods, some narrower and some wider within the above dimensional range, can be provided to afford more or less assistance in returning to the standing upright position.

Description—FIG. 3

FIG. 3 shows, in section, sleeves 16 fastened to fabric body 18, and the resililent rods nesting in the sleeves. The sleeves are made of nylon and are about 2 cm in diameter. The rods are from 4.8 mm to 8 mm in diameter and are made of fiberglass.

Operation—FIG. 3

Fabric sleeves 18 are loose fitting around rods 20. This loose fit allows the rods to travel slightly in the sleeves. Fabric body 18 and sleeves 16 remain somewhat independent of the rods, thus assuring ease of movement to the wearer. The diameter of sleeves 16 allows rods of up to 8 mm to be employed, all enjoying a loose fit. The rods are secured in place by a nylon flap 26 at the top of fabric body 18, and, can be readily removed or changed by moving the flap out of the way.

Description—FIG. 4

FIG. 4 shows the human figure in an upright, standing posture. My back support device can be seen to cover the entire back and buttocks. Fabric body 18 runs from top of shoulders to below buttocks. Straps 10, 12 and 22 harness fabric body 18 to torso. The entire combination constitutes a body harness. Straps 14 fasten body harness to upper legs. Advantages include freedom of movement and freedom from unnecessary loading of body parts.

Operation—FIG. 4

The standing figure is about to bend over. When he does so, the body harness will come into operation. In the standing position, the back support device is inert and the user experiences no loading. When user bends over, my back support device comes into operation as discussed below.

Description—FIG. 5

The bending over human figure has brought my back support device into operation. The resilient rods 20 and sleeves 16 are seen in a flexed position. The shoulder straps 10 are loaded. The leg straps 14 are loaded. The body harness spreads the load out over several areas of the upper body and is not uncomfortable.

Operation—FIG. 5

As the human figure bends over and the resilient rods 20 are flexed, the rods transfer load from the back to the upper legs. Shoulder straps 10 harness the torso. Abdominal strap 12 stabililzes the fabric body 18 (FIG. 1, 2, 3). Most importantly, leg straps 14 complete the load transfer from back to upper legs. Advantages include: complete or partial load transfer at user's choice. When bending over movement is in operation, the user's experience of load transfer is that of pleasant harness of the upper body and firm, sure, painless pressure on the upper thigh. Most importantly, back pain will be reduced or eliminated altogether.

SUMMARY, RAMIFICATIONS, AND SCOPE

The back support device is worn very lightly. It is predominately nylon mesh and is therefore self-cooling. While the user is in a upright posture, the appliance is hardly noticed. However, when a bending at the waist commences, the appliance goes into action and restrains the torso's movements. Waist bending movements load the resilient rods and torso straps, and the upper legs assume the burden ordinarily imposed on the lower back. The more one bends, the greater the support provided. One can change the size of the resililent rods and therefore select the amount of support one desires. For example, if the user's back is in pain, larger rods would provide greater relief. On the other hand, if the user's back is not painful, the user should use a smaller rod with correspondingly less support just to provide protection from, or prevent, back injury. The device thus provides back protection and support.

The reader will see that this appliance will have wide use. It is a simple and practical and inexpensive back support for people who bend over frequently in their jobs. Secondarily, anyone with back pain will benefit from it since it will ease the strain of bending-over activity. Also, it has no stiff or hard surfaces. When the user bends over, he or she will experience a gentle restraint to the torso, relief to the back, and a not unpleasant loading of the upper thigh.

The resilient rods (fiberglass) are available everywhere and are inexpensive. The appliance is of sewn fabric construction, and thus affords easy and inexpensive repair. One gets into and out of the back support device very easily, thus mitigating the nuisance factor.

One central principle of this device is the use of the resilient rods to transfer load from the back to the legs.

Ramifications of my back support device include the following: Some of its counterparts can be duplicated. For example, the fabric body and straps can be made of other materials and the 'harness' design altered somewhat. The resilient rods could be made of carbon fiber, for example.

The device can be made in many sizes, in a somewhat different shape, or of different materials and colors. Also, the resilient rods and sleeves and fabric body can be designed to be worn over the chest and abdomen.

This appliance will provide relief for many people who work in the trades, for anyone with back trouble, and for people recuperating from injury. The resilient rod load-transfer idea can be applied elsewhere on the human body. Thus, the scope of this invention will be larger than the examples provided and should be determined by the appended claims and their legal equivalents, rather than by the examples discussed above.

I claim:

1. A light weight, back strain relief harness for transferring stress from the back of a bending person to the upper legs and buttocks comprising: a harness having a back portion of a predetermined length and a predetermined width, said back portion having a shoulder end and a buttocks end, and adapted to substantially extend across the shoulders and the buttocks and down to just below the buttocks of the person; two adjustable loops to accommodate a user's upper legs connected to the buttocks end of said back portion; an adjustable belt to accommodate a user's waist connected to a mid-point on said back portion; two adjustable loops to accommodate a user's shoulder connected to said shoulders end of said back portion; and wherein said back portion further includes a plurality of resilient, normally straight rods approximately the same length as said predetermined length of said back portion, and spaced across said predetermined width of said back portion, whereby said resilient rods in combination with said back portion of said harness flex to transfer stress normally associated with back muscles to the upper legs and buttocks muscles when a person wearing said harness bends over, and assists the restraightening of the person as said flexed resilient rods restore to their normally straight form.

2. The back strain relief harness of claim 2 in which said plurality of resilient rods comprise: at least six fiberglass rods ranging from 4.8 mm to 8 mm in diameter.

3. The back strain relief harness of claim 2 in which said back portion of said harness comprises: a nylon mesh fabric having at least six, parallel sleeves attached lengthwise to the outside thereof to accommodate the insertion of said at least six rods.

4. The back strain relief harness of claim 2 in which said leg loops and shoulder loops comprise: relatively wide padded nylon straps adjustable by quick release fasteners.

5. The back strain relief harness of claim 2 which said adjustable belt comprises: a nylon strap that encircles the person, and is adjustable by quick release fasteners.

* * * * *